US006329000B1

(12) United States Patent
Ji

(10) Patent No.: US 6,329,000 B1
(45) Date of Patent: Dec. 11, 2001

(54) EXTRACT OF PINE NEEDLE AND THE USE THEREOF

(76) Inventor: Ling Ji, No. 5-400, Dong Da Street, Fengtai District, Beijing, 100071 (CN)

( * ) Notice: Subject to any disclaimer, the term of this patent is extended or adjusted under 35 U.S.C. 154(b) by 0 days.

(21) Appl. No.: 09/355,389

(22) PCT Filed: Jan. 27, 1997

(86) PCT No.: PCT/CN97/00006

§ 371 Date: Oct. 1, 1999

§ 102(e) Date: Oct. 1, 1999

(87) PCT Pub. No.: WO98/32455

PCT Pub. Date: Jul. 30, 1998

(51) Int. Cl.[7] .................................................. A61K 35/78
(52) U.S. Cl. ......................... 424/770; 424/773; 514/824; 514/866
(58) Field of Search ................................ 424/195.1, 770, 424/773; 514/824, 866

(56) References Cited

U.S. PATENT DOCUMENTS 5,204,369 * 4/1993 Valee et al. ........................... 514/456
5,466,453 * 11/1995 Uchida et al. ..................... 424/195.1

FOREIGN PATENT DOCUMENTS

| 93100041.6 | 1/1993 | (CN) . |
| 93111726.7 | 8/1993 | (CN) . |
| 93118751.6 | 10/1993 | (CN) . |
| 94105989.8 | 6/1994 | (CN) . |

OTHER PUBLICATIONS

Hu Yun et al; Effects of *Pinus massoniana* Lamb Leaves on the Life Span of *Drosophila melanogaster*, *Journal of Zhejiang College of TCM*, vol. 16, No. 6, 1992.

Hu Yun et al; Study of Effects of *Pinus massoniana* Lamb Leaves on Lowering Blood–Lipid, *Journal of Zhejiang College of TCM*, vol. 16, No. 3, 1992.

* cited by examiner

*Primary Examiner*—Christopher R. Tate
*Assistant Examiner*—Randall Winston
(74) *Attorney, Agent, or Firm*—Venable; Michael A. Gollin

(57) ABSTRACT

This invention discloses a kind of pine needle extract. The extract can be used to treat the following diseases: hypertension, coronary heart disease, angina pectoris, arrhythmia, diabetes, hyperlipemia, high blood viscosity, high blood aggregation, scleratheroma, cerebral infarction, brain scleratheroma, senile dementia, sudden deafness, etc.

24 Claims, 4 Drawing Sheets

EXTRACT OF PINE NEEDLE AND THE USE THEREOF

TECHNICAL FIELDS

This invention relates to an extract of pine needle and its uses in medicines, especially its use in treating hypertension and coronary heart disease. This invention also relates to a pharmaceutical composition comprising the extract of pine needle and its pharmaceutical uses.

BACKGROUND

Pine needle is also named pine leaf. Its Latin name is *Folium Pini*. One important thing is that Pine needle is leaf of plants of Pinaceae and Pinus. It comes from *Pinus tabuleaformis carr, Pinus massoniana Lams, Pinus Yuananensis Franch*, etc. In China there are 20 species and 10 varieties of Pinacaea plants, 16 species and 2 varieties have been planted.

In China, there has been a view that pine needle may be used as a supplement material for some medicines for many years. For example, some of the recipes collected in the Great Dictionary of Chinese Herbs can treat injury, edema, eczema, chronic bronchitis and asomnia, or prevent influzeza, epidemic encephalitis. Pine needle is used as one of the ingredients in these recipes.

Although pine needle has been used as a supplement material in medicines for a long time, it has never been reported that pine needle along has the effect of treating hypertension, coronary heart disease, angina pectoris, arrhythmia, cerebral infarction, hyperlipemia, high blood viscosity, high blood aggregation, arterial sclerosis, senile dementia and sudden deafness. It has never been reported that pine needle or its extract in combination of other substances can be used to treat the above diseases.

After study of many years, the inventor has found that an extract of pine needle can be used to treat hypertension, angina pectoris, myocarditis, arrhythmia, cerebral infarction, hyperlipemia, diabetes, high blood viscosity, high blood aggregation, arterial sclerosis, senile dementia, and sudden deafness. The effect is satisfactory. The new reliable uses of pine needle have been found.

BRIEF DESCRIPTION OF THE INVENTION

Therefore, one objective of the invention is to provide an extract of pine needle for treating many diseases, such as, coronary heart disease (CHD), angina pectoris, myocarditis, arrhythmia, hypertension, hyperlipemia, high blood viscosity, high blood aggregation, diabetes, cerebral infarction, cerebral arterial sclerosis, arterial sclerosis, senile dementia, and sudden deafness, etc.

Another objective of the invention is to provide a pharmaceutical composition for treating diseases.

Another objective of the invention is to provide a method for treating various diseases.

Another objective of the invention relates to use of an extract of pine needle in treating diseases.

The other objectives of the invention will be showed in the description of the invention.

According to the invention, an extract of pine needle has the colour of light brown to dark brown in solid state and shows the maximum absorption peak near 242 nm in the ultraviolet-visible light spectrum.

An extract of pine needle is used for treating myocarditis, CHD, angina pectoris, arrhythmia, hypertension, hyperlipemia, high blood viscosity, high blood aggregation, cerebral infarction, senile dementia, diabetes, cerebral arteriosclerosis, arterial sclerosis, and sudden deafness, etc.

DETAILED DESCRIPTION OF THE INVENTION

Figure 1:
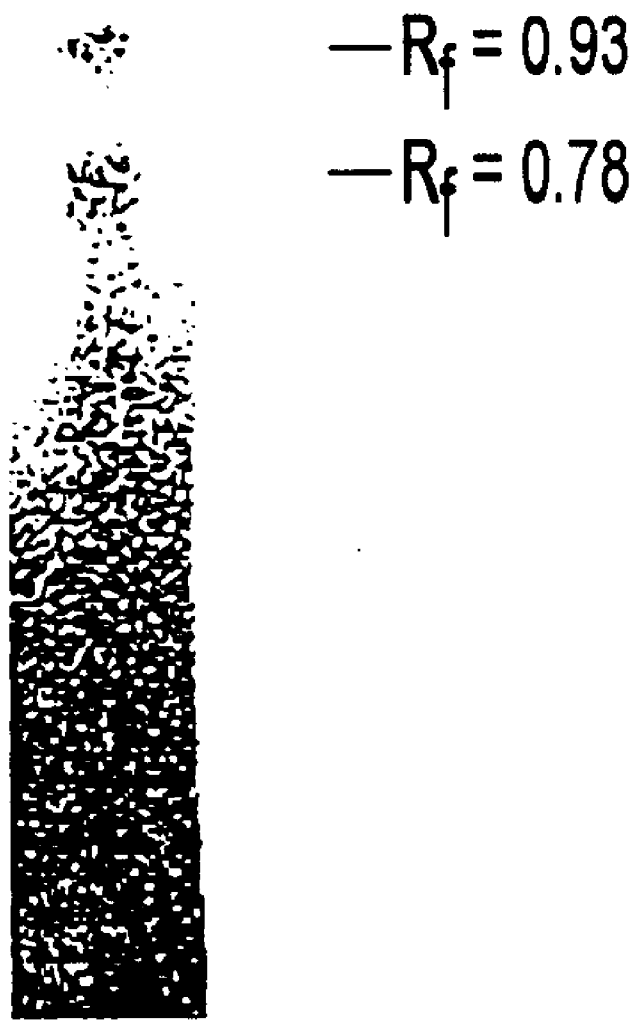
FIG. 1 shows the thin-layer chromatographic results of the extract of pine needle of this invention.

According to the invention, an extract of pine needle is light to dark brown in solid-state and water-soluble, and has a maximum absorption peak at about 242±1 nm in ultraviolet-visible light spectrum.

The inventor has found that the extract of pine needle has therapeutic effects in treating various diseases, including, such as, myocarditis, CHD, angina pectoris, arrhythmia, hyperlipemia, high blood viscosity, high blood aggregation, cerebral infarction, diabetes, cerebral arteriosclerosis, senile dementia, arterial sclerosis, and sudden deafness, etc. The extract of pine needle has particularly therapeutic effects on hypertension, hyperlipemia, high blood viscosity, and high blood aggregation.

In this invention, the extract can be extracted from pine needle using common methods. These methods include, for example, water-extraction method, water-alcohol method, alcohol extraction method and etc. Preferred is water-extraction method. The pine needle may be pine needle of various pine trees such as, *Dahurian Larch. Pinus tabulaeformis carr, Pinus massoniana Lamb, Cedrus deodata* (Roxb.) *Loud, Pinus pamila*(pull) *Regel, Pinus koraiensis Sieb.* et *Zucc., Pinus Yunnanensis Franch*, Japanese black pine and etc. The preferred pine needle is selected from *Pinus tabulaeformis carr, Pinus massoniana Lams* and *Pinus Yunnanensis Franch*.

The extract of pine needle is light brown to dark brown in solid-state. Whether the colour is light or dark depends on the method applied for drying. The extract is soluble in polar solvents such as water and alcohol, and its maximum absorption peak is found near 242 nm in the ultraviolet-visible light spectrum. Its $R_f$ values are 0.93 and 0.78 respectively when it is identified by using a thin-layer chromatographic analysis.

A pharmaceutical composition comprises a therapeutically effective amount of the extract of pine needle and a pharmacologically acceptable carrier or excipient.

The pharmacologically acceptable carrier or excipient is commonly used carriers/excipients.

A method for treating diseases, comprising the administration of therapeutically effective amount of the extract of pine needle of this invention to patients. These diseases include: hypertension, diabetes, CHD, angina pectoris, arrhythmia, myocarditis, hyperlipemia, high blood viscosity, high blood aggregation, cerebral infarction, senile dementia, arterial sclerosis, and sudden deafness.

The extract of pine needle of this invention is compatible with other drags in treating the above or other diseases. For example, it can not only lower blood pressure, blood-lipid, blood sugar, blood viscosity and the aggregation rate of platelet, but also regulate calcium metabolism when used together with calcium supplements.

The extract of pine needle can also be combined with other ingredients such as *Radix Puerariae, Ramulus Uncariae Cum Uncis*, pearl stratum powder, power of pearl, *Os Draconis, Concha Ostreae*, leaf of *Ginkgo biloba L., Radix Salviae Milliorrhizae, Flos Carthami, Rhizoma Chuanxiong, Fructus Trichosanchis*, leaf or cypress and etc. in treating the above diseases.

According to this invention, a formulation comprises pine needle and *Radix Puerariae* for treating the above diseases. The proportion of pine needle and *Radix Peurariae* is 3:1–5:2, preferably, 3:1–4:1. According to the invention, the formulation further includes powder. The ratio between pine needle and pearl stratum powder is 20:1–2:1. the proportion of pine needle, *Radix Puerariae* and pearl stratum powder is preferably 18:6:9. The regulation effect of calcium metabolism can be increased when pearl stratum powder is added to the formulation.

*Radix Puerariae* is the root of *Puecraria Lobata* (Wild) *Ohwi*, and pearl stratum powder is made from the inner parts of shells of *Cristavia plicata* (Leach) or *Aaadonta woodiana* (lea.). *Radix Puerariae* and pearl stratum powder have wide sources are available from the market.

According to this invention, a pharmaceutical composition comprises an effective amount of the extract of pine needle and *Radix Puerariae*, and a pharmacologically acceptable carrier/excipient.

A therapeutic method comprises the administration of therapeutically effective amount of the extract of the formulation for treatment of the above diseases.

The extract of pin needle and *Radix Puerariae* can be extracted from the mixture of these two herbs, and it may be obtained by mixing the extract of pine needle and the extract of *Radix Puetariae*.

The pharmaceutical compositions of this invention can be delivered by oral administration or topical application. They can be produced in various kinds of dosage forms, such as, tablets, oral solutions, powders, pellets, capsules, injection (including intravenous injection), lotions for external application, Gao, tincture, pulveres, and infusions, etc.

The dosages of the extract of pine needle are, in oral administrations: 1–3 g per time for adults, preferably 1–2 g per time, three times a day, and 0.5–1 g per time, three times a day for children aged at 5–14 (above 5 years old and below 14 years old).

Now as an example, we will describe in details the process of making the extract of pine needle by using water-extraction method.

Take pine needle as a raw material. The pine needle can be processed in whole or be cut into segments or triturated into powder before processing. It is preferred to cut pine needle into segments before treatment. Add excess water into pine needle. The water added is at least 4 times (by weight), preferably 8–9 times, of the pine needle. The mixture is heated to boiling for extracting. The time period for boiling is 1–2 hours and preferably 1.5 h. The mixture is filtered after extracting and then condensed to give a concentrated solution in dark brown.

The residue from the filtration may be extracted for second time by being added with water and boiling. The added water is at least 3 times by weight of the residue, while 6–7 times is preferred. The time for boiling it 0.5–1.5 hours, preferably 1 h. After the filtration of second time, The filtrate of the second time can be combined with the filtrate of the first time and then they can be condensed together to get the condensed solution.

If necessary, the condensed solution can be dried to give powder in light to dark brown. Many methods such as spray drying method, vacuum drying method, and freeze drying method, etc. can be used for drying. The higher the temperature applied during the drying process, the darker the colour of the powder.

Identification Test for the Extract of Pine Needle

1. Identification Test by Using Thin-Layer Chromatography (TLC)

5 g of the dry extract powder of pine needle was weighed and ethyl ether was added to immerse it for 2 times, 30 ml, 1 hour for each time (keep shaking). After filtering, the filtrates of these two times were pooled together, ethyl ether was retrieved to get dry substance. A little of ethyl ether was added to dissolve the dry substance, and the solution was transferred into a volumetric flask with a capacity of 1 ml. Added ethyl ether to get a solution of 1 ml and shake evenly. Took the solution as the sample to be tested. Tested the solution with TLC according to the method published in the Chinese Pharmacopoea (edition: 1995, appendix FIB): Took 10–20 $\mu$l of the above solution to be tested. Dot it onto the thin-layer plate of Silica G with sodium carboxymethylcellulose as the adhesive. Used petroleum ether and ethyl acetate (ratio of 4:1) as the developer. Developed the spot into 12 cm. Took it out and air dry. Sprayed a solution of sulfuric acid in alcohol with the concentration of 20% on it and then heated it at 105° C. until the color of the spot was developed. There were same two main spots of violet red in color among the chromatography of the tested solution. The values of $R_f$ were 0.93 and 0.78, respectively (see the attached FIG. 1).

2. Identification Test by Using Ultraviolet Spectrum

Made the extract powder of pine needle through a sieve of 60 mess. Then dried it at 50° C.–55° C. for 3 hours. Then moved it into the solica dryer for storage and use.

Weighed 2 g of the pre-treated extract of pine needle (Notice: The accuracy is required to be 0.01 g). Put it into a triangular flask of 50 ml with a plug. Added petroleum ether 14 ml each time, 3 times in all and 30 minutes for each time to extract with ultrasonication. Then took the mixture for filtration. The solvent was volatilized to get the residual dregs. Added chloroform to the dregs for extraction with ultrasonication, 15 ml and 30 minutes for each time, 3 times in all. Then took it for filtration. Pooled the filtrates, Retrieved chloroform to get the dry substance. Added a little of chloroform to make the dry substance dissolved. Moved the solution to a volumetric flask with a capacity of 10 ml. Added chloroform to the scale. Shook it evenly and used as sample to be tested.

Used ultraviolet spectrophotometer (Model VV-260, Shimadzu, Japan):

The width of the gap: 1 nm;

The increment of wavelength: 2 nm;

The range of wavelength: 200–500 nm;

The range of absorptance: 0–1.

Figure 2:
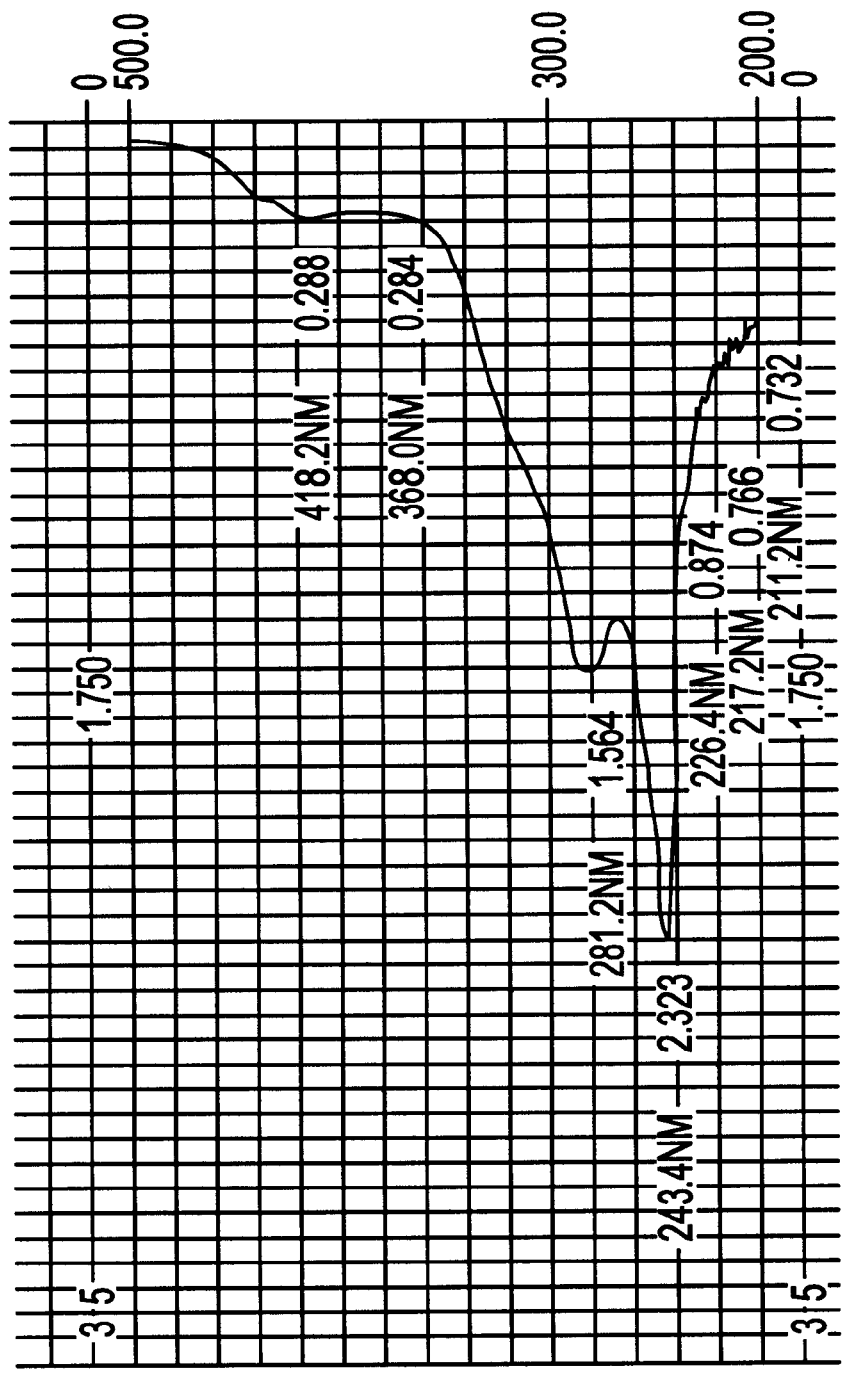
FIG. 2 shows the ultraviolet-visible light absorption graph of the extract of pine needle of this invention.
Figure 3A:
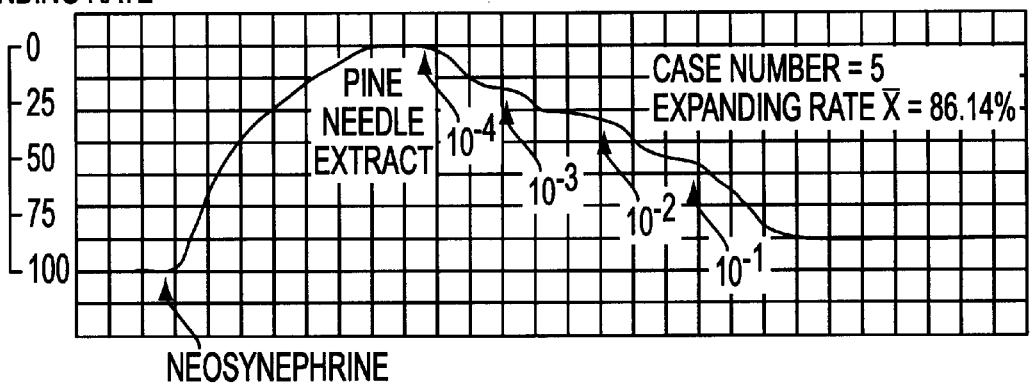
FIG. 3a shows the dependent relationship between the vasodilation capability and the dose/concentration of the extract when endothelium exists.

Diluted the tested solution appropriately to make its absorptance being 0.6–0.8 at its maximal absorption wavelength. According to the spectrophotometric method published in the Chinese Pharmacopoeia (Edition: 1995, appendix VA), the ultraviolet-visible spectrum detected in the wave length ranges from 200 nm to 500 nm (see attached FIG. 2) showed the maximal absorption peak appears at the wavelength 242±1 nm.

1. The Hypotensive Effect of the Extract from Pine Needle

The extracts of Pine needle (decoction, spray drying powder after concentration or water extraction-alcohol deposition) showed significant effect of decreasing blood pressure on the patients with primary hypertension or renal hypertension and the rats with spontaneous hypertension (SHRsp) or renal hypertension by one-clamp of the two renal arteries. This effect was dose-dependent.

1.1. Acute Decreasing Blood Pressure Test of the Extract from Pine Needle 1.1.1. Materials and Methods:

Experimental animals: 30 male Wistar rats in good health, wherein 20 of them were operated to form renal hypertension by one-clamp of one renal arteries according to Goldblatt method; 30 male rats with spontneous hypertension (SP).

Drug: the extract powder of pine needle, compound Folium Apocyni Veneti tablet.

Normal control group: administrating extract powder of pine needle, 1.6 g/kg/time.

Blank control group: (SP) administrating distilled water, 2 ml/100 g (body weight)/time.

Positive control group: administrating compound Folium Apocyni Veneti tablet, 1.08 g/kg (body weight)/time.

Low dose group: administrating the extract powder of pine needle, 0.83 g/kg (body weight)/time.

High dose group: administrating the extract powder of pine needle 3.3 g/kg (body weight)/time.

Isolated the right common carotid artery after the animal was anesthetized. Ligated the distal end of the right common carotid artery and inserted the heparinized catheter into the proximal end. Connected the catheter with a five-lead physiological instrument, and monitor the blood pressure ad the heart rate. Opened the abdominal cavity. Administrated the drug via the duodenum. Observed the changes of blood pressure and heart rate before administrating the drug, 30 minutes, 1 hours, 2 hours, 3 hours after administrating the drug.

1.1.2. Results: (See Table 1)

(1) Blood pressure of the normal group was decreased slightly at 30 minutes after the administration, but restore to the original level at 1 hour after the administration (P>0.05). (2) No obvious change of blood pressure in blank control group (P>0.05). (3) Blood pressure of positive control group began to decrease at 30 minutes after the administration, the hypotensive peak appeared at 2 hours after the administration, the decreasing rate was up to 8.1±1.22%, and there was statistical significance compared with the blood pressure before the administration (P<0.05). (4) Blood pressure of the low dose group began to decrease at 30 minutes after the administration. The hypotensive peak appeared at 2 hours after the administration. The decreasing rates were up to 14.3±2.32% (the group with renal hypertension.) and 15.6±2.17% (the group of SP), respectively, there is very significant difference compared with that before the administration (P<0.01). (5) Blood pressure of the high-dose group was decreased most significantly at 2 hours after the administration. The decreasing rates were up to 18.6±2.07% (the group with renal hypertension) and 17.6±1.98% (the group with SP), respectively. Moreover, there are very obvious differences compared with the blood pressure of this group before the treatment (P<0.001) and that of the other group at 2 hour after the treatment (P<0.001).

SUMMARY

Acute decreasing blood pressure test of the extract of pine needle showed that the extract of pine needle had no obvious effect on the blood pressure of normal rats, but it could decrease significantly the artery pressure of the rats with SP and renal hypertension. The effect appeared at 30 minutes after the administration. The hypotensive peak appeared at 2 hours after the administration. The effect could last for 3 hours or more and was dose-dependent. The effect of decreasing blood pressure of the extract was stronger than that of compound Folium Apocyni Veneti tablet.

1.2. Long-Term Decreasing Blood Pressure Test of the Extract from Pine Needle 1.2.1. Materials and Methods:

10 male Wistar rats in good health, 50 male rats with spontaneous hypertension (SP). Drug: same as that of the acute decreasing blood pressure test.

Methods: Wistar rats (1) normal control group: administrating the extract powder of pine needle, 1.6 g/kg (body weight)/d. Every 10 SP rats made a group; (2) blank control group: administrating distilled water 2 ml/100 g (body weight)/d. (3) compound Folium Apocyni Veneti group: 1.08 g/kg (body weight)/d. (4) Low dose group: 0.83 g powder of pine needle /kg (body weight)/d. (5) moderate dose group: 1.6 g powder of pine needle /kg (body weight)/ d. (6) high dose group: 3.3 g powder of pine needle /kg (body weight)/d. Gavage once a day. The volume of gavage was 2 ml/kg (body weight) each time. 3 weeks made up a course of treatment. Examined the blood pressure and the general state of the rats before and after the drugs given. Determined the blood pressure in vitro and the carotid blood pressure, then tested the data with Linear Relation-Regression analysis. Showed the results in the form of Mean±Standard Deviation (K±SD). then tested the difference existing between every two groups.

1.2.2. Results: (See Table 2)

After the treatment with the extract powder of pine needle, the general states of the rats were normal. Body weights f the rats in blank control group increased 2 g on average while that of the rats in high, moderate and low dose groups increased 6.7 g on average. The extract of pine needle had no effect on the blood pressure of normal control group. The decreasing rates of blood pressure in low dose group, moderate dose group and high dose group were 30.7±0.93%, 38.82±3.68% and 48.22±1.16%, respectively. In these three groups, there is very significant difference compared with the blood pressure before treatment. (P<0.001), while remarkable difference compared with blank control group and Folium Apocyni Veneti group (P<0.001). The MAP after the treatment showed significantly positive relation with the blood pressure in vitro (r=0.903, t=8.899 P<0.001).

Conclusion: The extract of pine needle had a satisfactory effect of decreasing blood pressure on rats (SP). The effect was dose-dependent. The extract had no impact on normal blood pressure. Its effect of decreasing blood pressure was stronger than that of compound Folium Apocyni Veneti tablet (P<0.001). The activity and appetite the SP rats after the treatment by the extract were normal, and their body weight increased significantly.

1.3. Clinical Test of the Decreasing Blood Pressure Effect of the Extract from Pine Needle 1.3.1. Methods:

Selected 106 in-patients and 38 out-patients for the test. After inquired the medical history intensively, gave physical examination and laboratory examination, 124 patients were diagnosed as essential hypertension (EH) according to the diagnostic standard of hypertension worked out by WHO expert association, including 38 patients of primary EH, 71 of secondary EH, 15 of tertiary EH and 20 of renal hypertension. The patients had stopped taking hypotensor, diuretic and vasodilator for more than a week before involved in the test. They were divided into two groups, that is, the treatment group and the control group.

Patients of the treatment group took orally the extract of pine needle (in the form of oral solution) 15 ml each time, three times a day, one month/course of treatment, patients of the control group took compound Folium Apocyni Veneti tablet, 2 tablets each time, three times a day, one month/course of treatment. Determined the blood pressure of all the patients in the morning of three days before and after the administration, respectively. These three days must be he days other than the day on which the drug was administrated. Took the means as the blood pressure before and after treatment respectively. (Notice: every 15 ml of the oral solution contained 1.6 g of the extract from pine needle.)

The standard for judging the effect of decreasing blood pressure:

(1) Remarkable effectiveness: meeting either of the two requirements as follows: <1> Made the diastolic pressure normal with decreasing it by more than 10 mmHg. <2> Made the diastolic pressure lowered by 20 mmHg or more although the diastolic pressure didn't become normal.

(1) Effectiveness: meeting one of the three requirements as follows: <1> Made the diastolic pressure normal with decreasing it by less than 10 mmHg. <2> The diastolic pressure was 10–19 mmHg lower than before treatment, but it still didn't become normal. <3> The systolic pressure was at least 30 mmHg lower than before treatment.

(3) Ineffectiveness: Not meeting any of the above standards.

1.3.2. Results: (See Table 3)

There were no significant differences in the ages and the blood pressures before the treatment of these two groups (P>0.05). When compared the blood pressure before and after the treatment, the blood pressure in the treatment group was decreased most significantly (P<0.001), while the blood pressure in the control group was lowered slightly (P<0.05). There is obvious difference between the treatment group and the control group. Both of the remarkable effective rate and effective rate of the treatment group are significant that these of the control group (P<0.001 or P<0.05).

During the test, it was also observed that the symptoms such as dizziness, headache, chest distress, palpitation, insomnia, dysphoria in chest palms-soles were relieved significantly or disappeared in the treatment group. The remarkable effective rate of the treatment group was up to 52.41–75.22%, which was obviously higher than that of the control group. (P<0.001). No adverse reaction was observed. No abnormality of blood routine, urine routine, stool routine, liver function and renal function was observed. The renal function was improved more or less among the 20 patients with renal hypertension. The urea nitrogen and creatinine in blood declined and isotope renogram showed that the renal excretory function was improved than before treatment.

Conclusion: The extract of pine needle had remarkable therapeutic effect on essential hypertension and renal hypertension. Its effect of decreasing blood pressure, relieving clinical symptoms and improving renal function was remarkable super than that of the control group (compound Folium Apocyni Veneti).

2. The Hypolipidemic Test of the Extract from Pine Needle 2.1. Materials and Methods:

Experimental animals: 60 Beijing white rabbits with big ears, all male with body weight of 1.5–2 kg.

Drugs and reagents: cholesterol (produced at Beijing Chemical Reagent Company). Propyl thiooxyuracil tablet (refers to PTV hereafter, produced in Germany, 50 mg each tablet), lard (prepared by ourselves). The extract powder from pine needle of the invention (refers to the power of pine needle hereafter). Inostitol hexanicotinate tablet (produced by the second Pharmaceutical Factory of Beijing, 0.2 each tablet). The kits of total cholesterol, triglyceride, high density lipoprotein, and low density lipoprotein (produced by Beijing Zhongsheng Biotechnical Company).

Methods: The white rabbits with big ears were divided into 5 groups at random after raised for 10 days with normal diet. 10 rabbits each group. The high fat diet was given after taking blood from the helicine veins of the fasting rabbits in the morning. Determined the blood-lipid of the blood samples. The high fat diet included cholesterol 2 g/kg (body weight)/d, lard 0.5 g/kg/d, PTV 12.5 mg/kg/d. In the forth group, gave 075 g/kg/d of the powder of pine needle along with the high fat diet to the rabbits of (the prevention group). Took blood from the fasting rabbits again and determined their body weights after 15 days of high-fat diet. Then stopped the high-fat diet and changed it for normal diet: (1) blank control group: giving distilled water 10 ml each day with the gavage method; (2) positive control group: giving Inositol hexnicotinate tablets, 0.3 g/kg/d; (3) low dose group: giving the powder of pine needle, 0.25 g/kg/d; (4) prevention group: went on giving the powder of pine needle 0.75 g/kg/d, 30 days in all; (5) high dose group: giving the powder of pine needle, 1.5 g/kg/d. The powder was dissolve din 10 ml distilled water and gave it with gavage method once a day. Took blood from the fasting rabbits on the fifteenth day after the administration to determine the levels of blood-lipid. The levels of total cholestorol, triglyceride, high density lipoprotein and low density lipoprotein were examined by CHOO-PAP method, GPO-PAP method, PTA-$Mg^{2+}$ deposition method and PVS one-step deposition method, respectively. The instrument used was Hitachi, Model 750 automatic biochemical analyzer.

2.2. Results: (See Table 4)

From table 4, we could learn that there was no statistical difference among various indexes of the blood-lipid of all the groups before the high fat diet given (P>0.05). However, after the high fat diet given, the levels of total cholestovol, triglyceride, and low deasity lipopratein in Group 4 (prevention group) were obviously lower than that in the other four groups, and the differences showed remarkable statistical significance (P<0.001). The levels of total cholesterol, triglyceride and low density lipoprotein were decreased after the treatment in all the groups. Remarkable statistical significance existed when compared their levels of Group 1 with that of the other four groups after the treatment. Their levels after treatment were lowered most obviously in Group 4 (P<0.001). The decreasing rate of Group 1 was significantly different from that of the other four groups. The decreasing rates in groups 3, 4 and 5 is super compared with that in Group 2. The decreasing rate of triglyceride in Group 2 showed no statistical difference when compared with that in Group 1, but showed statistical difference when compared with that in Group 3, 4, 5, and wherein the most significant difference appears in Group 5 (P<0.001). The decreasing rates of low density lipoprotein in Group 3, 5 were most significant (P<0.001). The levels of high density Lipoprotein declined in Groups 1 and 2, while increased in Groups 3, 4 and 5 after the treatment, wherein the increment in Groups 4 and 5 are more significant, while that in Group 5 was most significant (P<0.001).

Conclusion: For the animals with hyperlipemia due to high fat diet, the extract of pine needle could lower the levels of serum total cholesterol, serum triglyceride, serum low density lipoprotein, while made the levels of serum high density lipoprotein increased. The therapeutic effect was most satisfactory in the prevention group, then followed by the high dose group. All of these proved that the extract of pine needle had therapeutic and preventive effect on hyperlipemia.

3. The Test for the Extract of Pine Needle to Regulate Parathyroid Function 3.1. Materials and Methods:

Experimental animals: 5 male wistar rats in good health with body weight of 320–360 g; 10 male SP rats with body weight of 170–270 kg. Experimental reagents: the extract powder of pine needle, the radio-immunity kits of parathonmone (PTH) and calctionium (CT) produced at Rongyan company of Japan.

Methods: The animals were divided into: ① normal control group; ② SP blank control group; ③ SP treatment group, five rats a group. Wistar rats is (1) normal control group: gave the powder of pine needle, 1.5 g/kg (body weight)/d. SP rats were divided into 5 groups, 5 rats a group; (2) blank control group: gave distilled water 2 ml/100 g (body weight)/d with the gavage method; (3) compound Folium Apocyni Veneti group: 1.08 g/kg (body weight)/d; (4) Low dose group: gave the powder of pine needle 0.8 g/kg/d. (5)moderate dose group: gave the powder of pine needle 1.5 g/kg/d; (6) high dose group: gave the powder of pine needle 3.0 g/kg/d, once gavage a day, the volume of gavage fluid was 2 ml/100 g (body weight). 3 weeks/a course of treatment. Made the rats anesthetized and took blood from the eyeball vein before and after the treatment. Isolated the serum by freezing and cetrifugation the blood (−4° C.). The serum PTH and serum CT were determined using radio-immunity method.

3.2. Results: (See Table 5)

From table 5, we could learn that before treatment, significant difference existed between the values of PTH and CT in Group 1 (normal control group) and that in Groups 2 and 3. After the treatment, the levels of PTH declined significantly while that of CT increased remarkably in Group 3. But as the levels of PTH and CT, difference still existed between Group 1 and Groups 2 and 3 (P<0.05). After the treatment, significant difference existed between the decreasing values of PTH and the ascending values of CT in Group 3 and these in Group 1 and 2. (P<0.05 and P<0.001).

CONCLUSION

The extract of pine needle has an effect in a certain extent on the parathyroid function of SP rats. The PTH levels of SP rats declined while the CT levels increased significantly after 3 week's treatment. Although after the treatment, difference existed comparing with that in normal control group, statistical significantly difference existed when compared the decreasing rate of PTH and ascending rate of CT with that in blank control group. All of these proved that the extract could regulate the parathyroid function of SP rats to some degree.

4. The Effect of the Extract from Pine Needle on the Hemorheology 4.1. The Test for the Extract to Inhibit Platelet Aggregation 4.1.1. Materials and Methods:

Experimental animals: 25 male Beijing white Rabbits with big ears in good health, their body weights 1.5–2 kg.

Reagents and Instruments: Extract of pine needle, Danshen (*Radix Salviae Miltiorrhizae* injection solution, containing 2 g crude drugs each ml), the extract of *Radix Puerariae*, containing 2 g crude drugs/ml), ADP (20 μg/200 μl), Phosphate buffer (0.2 mol/l, 300 mg/ml), Sodium citrate solution (3.8%), 2% silicone-petroleum ether solution, Model MG-576 platelet aggregation instrument, Desk model balancing automatic recorder, Round colorimetric cup (Model: CHRONO-LOG312'), silicified centrifuge tube, Microsampler.

Methods: Took 3 ml blood from the helicine veins of the rabbits with empty stomach for 10–14 h. Put blood into silicified centrifuge tube. The proportion of the blood and sodium citrate solution was 9:1. Mixed them and took the mixture for centrifugation (800 rpm). After 4 minutes, took out the upper layer fluid which was platelet-rich plasma (PRP). The residual blood was centrifuged (3000 rpm) for 10 minutes. Took out the supernatant which was plasma-pool platelet (PPP). Tested the platelet aggregation ability with BORN turbidimetry at constant temperature of 37° C. The volume of plasma in the colorimetric cup was 250 ml. The test time was 5 minutes. Samples were divided into several groups: ① ADP+phosphate buffers, ADP 2 μmol/L, phosphate buffer 0.2 ml/L; ② ADP+*Radix Salviae Miltiorrhizae* injection solution with the same volume; ③ ADP+ the extract solution of *Radix Peurariae* with the same volume; ④ ADP+the extract solution of pine needle with the same volume; ⑤ ADP+the composition solution with the same volume.

2. Results (See Table 6)

From table 6, it could be observed that the platelet aggregation rates of Groups 2, 3, 4 and 5 declined obviously and their decreasing rate, especially groups 4 and 5, had very significantly difference compared with that of Group 1. The 1' rate of aggregation inhibition was up to 74.56–80.06%. The 5' maximal rate of aggregation in the Groups 4 and 5 also showed significant difference compared with that in the Groups 2 and 3.

3. Conclusion:

The test of platelet aggregation inhibition in vitro showed that the composition, the extract of pine needle and the extract of Radix Puerariae could inhabit the platelet aggregation obviously, which were significantly stronger than that of the Danshen solution of the same concentration. Their effects of inhibiting aggregation were the strongest at 1'. The strongth of the effects of inhibiting platelet aggregation in turns: composition group>the extract of pin needle group>the extract of Radix Puerariae group>Danshen group. The test showed that either the composition consisting of pine needle and Radix Puerariae or the extract of pine needle had important impacts on preventing platelet aggregation and treating blood stasis.

4.2 Clinical test for the extract of pine needle to improve hemorheology

1. Materials and Methods:

87 patients aged 37–75 took part in the test, including 52 male patients and 35 female patients, wherein 36 patients with coronary heart disease, 37 patients with hypertension, 9 patients with cerebral infarction, 45 patients with hyperlipomia, 12 patients with diabetes (some patients suffered from 2 diseases or more). The control group included 44 patients, wherein 18 patients with CHD, 21 patients with hypertension, 3 patients with cerebral infarction, 32 patients with hyperlipemia (Some patients suffered from 2 diseases or more). The patients had stopped taking the drugs which had effects on the hemorherlogy such as dipgridamok, Danshen, Aspirine, $Ca^{2+}$-blocker agent for more than a week before taking part in the test.

The oral solution of the extract from pine needle was given 15 ml (containing 1.6 g the extract of pine needle) each time, three times/day, one month/a course of treatment, in the treatment group. 3 tablets each time of the compound Danshen tablet were given, three times/day, one month/ a course of treatment, in the control group. Determined the indexes of hemorheology before and after the treatment. Tested the statistical significance of the means of the results. T-test was used to determine the statistical significance of the means of every two groups.

4.2.2. Results:

After the treatment, erythrocyte sedimentation rate (ESR) was slowed down and haematocrit was reduced. The specific viscosity of plasma and that of whole blood (high shear, low shear) were improved remarkably. The rate of platelet aggregation was lowered significantly (see table 7 and table 8).

CONCLUSION

The extract of pine needle had obvious therapeutic effect on the patients and animals with hyperviscosity of hyperaggregation. It could reduce the ESR, haematocrit, specific viscosity of plasma and whole blood as well as the platelet aggregation rate. This was very important for quicken the blood and transform stasis, and for preventing or treating thrombotic diseases as well as improving the microcirculation. Thus, this provided the theoretical basis was for the drug to treat myocardiac inforction, coronary heart disease, Angina pectoris, cerebral infarction, hypertension, thrombotic diseases of arteria and vein, sudden deafness, and blood stasis.

5. Clinical test for the extract of pine needle to enlarge the coronary artery and against angina pectoris, arrhythmia 42 patients with coronary heart disease took part in the test, gave each of them the extract of pine needle 15 ml (containing the extract of pine needle 1.6 g) each time, three times a day. Examined the EKG, blood-lipid, $TXB_2$, $PGI_2$ before and after the treatment. The patients in the control group took orally isosorbide dinitrate 10 ml each time, three times a day, one-month a course of treatment.

Results: (see tables 9, 10 and 11)

Among the 42 patients with CHD in the treatment group, 7 patients were suffering from frequent ventricular premature beats, which the premature beats of 6 patients of them were reduced obviously and 1 patient was not effected after the treatment with the extract; 7 patients with frequent atrial premature beats: the obvious effect was showed in one case; 24 patients with chronic coronary insufficiency: the St-T segments of ECG were improved in 16 cases; 4 patients with chronic coronary insufficiency accompanied by remote mycardial infaction: the obvious therapeutic effect was showed in 1 case since that the ECG became almost normal, improved ST-T segments of ECG were showed in 2 cases, no effect was showed in the residual one case; the blood sugar and the urine sugar of the 15 patients with diabetes were reduced significantly ant their sympotoms such as limb numbness, thirsty, diuresis were improved remarkably.

To control angina pectoris: The total incidences of angina pectoris among the 42 patients in the treatment group were reduced to 128 times a week after the treatment from 395 times a week before the treatment (P<0.001). None of them showed aggravated symptoms. The total effective rate of the treatment group was up to 92.8%. The total incidences of angina pectoris in the control group were reduced to 108 times a week after the treatment from 215 times a week before the treatment. (P<0.05). The total effective rate of the control group was up the 86.6%.

Conclusion: The extract of pine needle could reduce the incidences of angina pectoris significantly, improve the ischemic change of ECG, control the incidences of arrhythmia (ventricular premature beats), lower the level of sterum total cholesterol significantly, lower the level of serum triglyceride slightly, raise the level of serum high density lipoprotein, reduce the level of $TXB_2$, and raise the level of $PGI_2$. Therefore, the extract could increase the blood flow volumes of cerebral arteries, reduce the mgocardial oxygen consumption volume and reduce the mgocardial post-load so as to protect the ischemic mgocardium.

6. The effect of the extract from pine needle on inhibating senility and increasing cerebral blood flow 25 patients with cerebral infarction or senile dementia were received the treatment of oral solution of pine needle. Examined the REG (Rheology Encephalogram, REG), serum lipid peroxide and serum copper-zinc superoxide dismutase (refers to $SOD_1$ hereafter) before and after the treatment. The method for administration was as follows: 15 ml (containing the extract of pine needle 1.6 g) each time, three times a day, 3 months a course of treatment. After the treatment, the REG was improved significantly, the level of $SOD_1$ was decreased and that of lipid peroxide was reduced remarkably. (see Table 12)

The REG before the treatment showed the increased vascular resistance, the reduced volume of blood flow, the slowed blood flow rate and the decreased vascular elasticity. However, among the 25 patients who received the treatment of pine needle, 20 patients showed remarkable improvement of the REG, including reduced vascular resistance, accredited blood flowing, increased volume of blood flow and improved wave shape. All of these proved that the extract of pine needle could increase the volumes of cerebral blood flow.

7. The blood vessel-dilation effect of the extract from pine needle

The isolated perfusion test of dialing vascular circular proved that the extract of pine needle cold expand arteries. The effect was endothetium-dependent and dose-dependent. When endothelium existed, the higher the dose of the extract, the stronger the effect of vascular-dilation. The maximal dilation rate was up to 86.88±12.03%. Without endothelium, the extract could only expand the vessel slightly even at the highest concentration (14.23±2.06%). These proved that the extract of pine needle expanded the blood vessel by regulating vascular active substances of endothelium (see attached FIGS. 3a–3d).

EXAMPLE 1

Preparation of the oral solution of pine needle:

Took 10 kg pine needle, added 80 kg water to it. Decocted the mixture for 1.5 h. Took out the decocted soup. Added 60 kg to the decocted dregs. Decocted the mixture for 1 h. Took out the decocted soup of the second time. Combined the soup of there two times together. Filtered the soup. Added alcohol to the filtrate. After standing the mixture for 24 hours, discarded the sediment, retrieved the alcohol. Concentrated the liquid into a solution of 10 kg. Added distilled water to dilute it into a solution of 20 kg. Added a little of stevioside and the preservative nipagin to the soup. Packed the solution into the bottles. Each bottle contained 10 ml the solution.

EXAMPLE 2

Preparation of the capsules of pine needle:

Took 10 kg pine needle and 3.5 kg Radix Puerariae. Added water of 5 times volume. Decocted the mixture for 2 hours, filtered the mixture. Then took out the dregs of decoction and added water the volume 4 times. Decocted the mixture for 1.5 h. Filtered it to get the soup. Combined the soup of these two times together. Added alcohol to the combined soup. Discarded the sediment after standing the mixture for 24 h. Retrieved the alcohol. Then concentrated the soup into an extractum. Dried the extractum to get the dry extractum. Smashed it into powder for later use. Then 5 kg pearl stratum power and smashed it. Sieved it into fine powder. Mixed it with the above powder of the extractum. Used the automatic capsule fill machine to fill the capsules with the powder. Each capsule contained 0.5 g drug powder. Packed it with plastic-aluminum foil.

EXAMPLE 3

Preparing method:

Took 1800 g pine needle and 600 g Radix Peurariae. Added water to the mixture of them. Decocted the mixture for two times: 8 times volume of water for the first time and decocted the mixture for 1.5 h; 6 times volume of water for the second time and decocted the mixture for 1.5 h. Filtered the mixture. Combined the filtrate of these two times together. Dried the combined filtrate to get the powder.

Now we will describe the animal test and the clinical test of the composition consisting of the extracts from pine needle of the invention and that of Radix Puerariae (refers to "the composition" hereafter).

8. The effect of the composition to expand blood vessel

Figure 4:
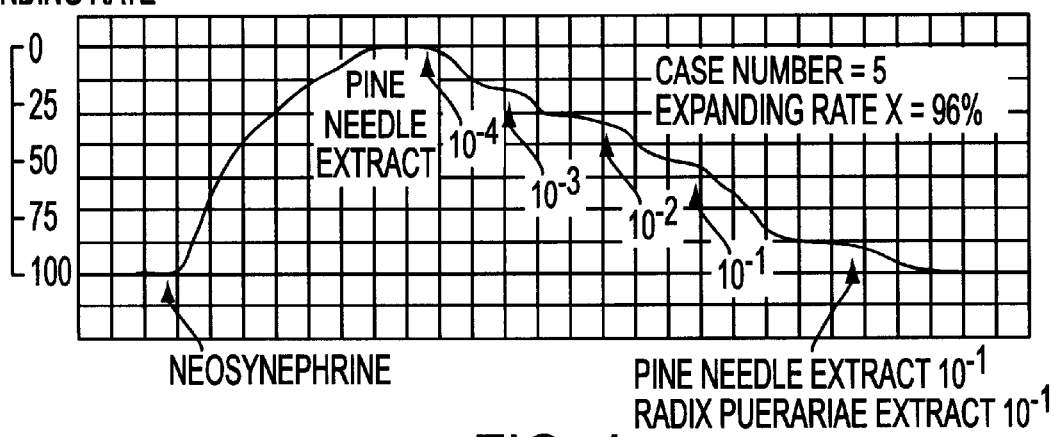
FIG. 4 shows synergetic effect of the extract of pine needle and the extract of Radix Puerariae when endothelium exists.
Figure 3B:
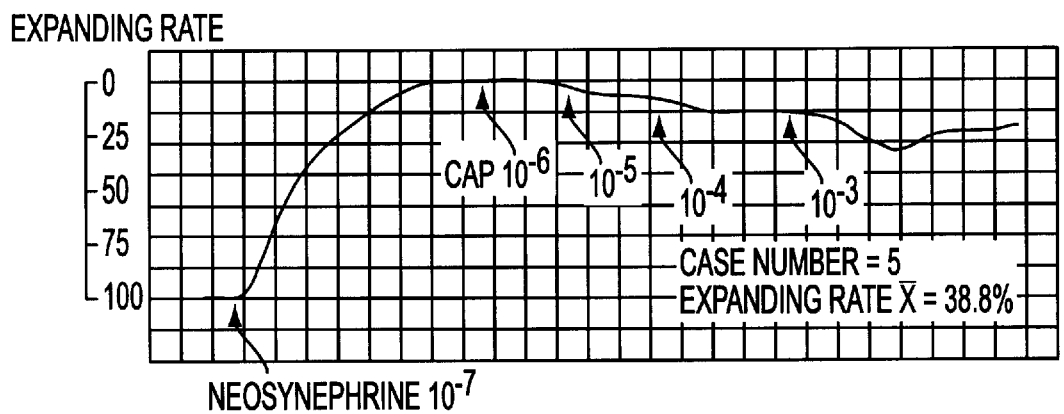
FIG. 3b shows the relationship between vasodilation capability and dose/concentration of Capoten as the control group when endothelium exists.
Figure 3C:
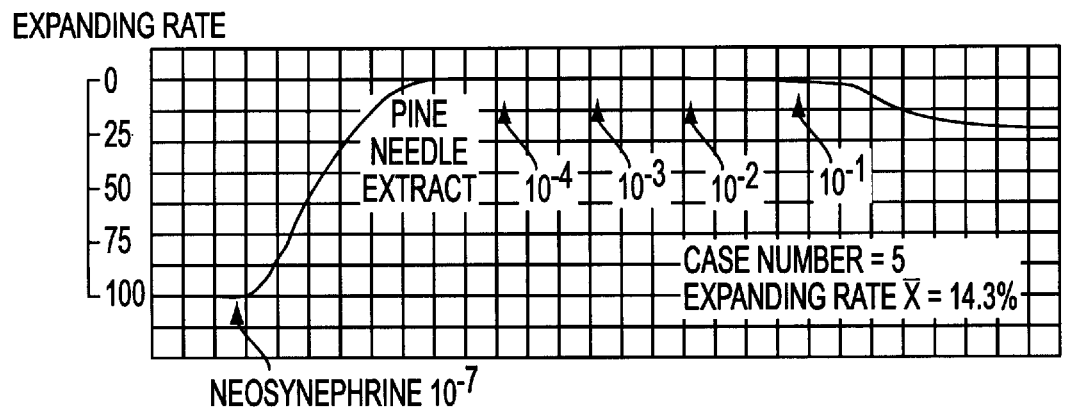
FIG. 3c shows the relationship between vasodilation capability and dose/concentration of the extract of pine needle when endothelium is removed.
Figure 3D:
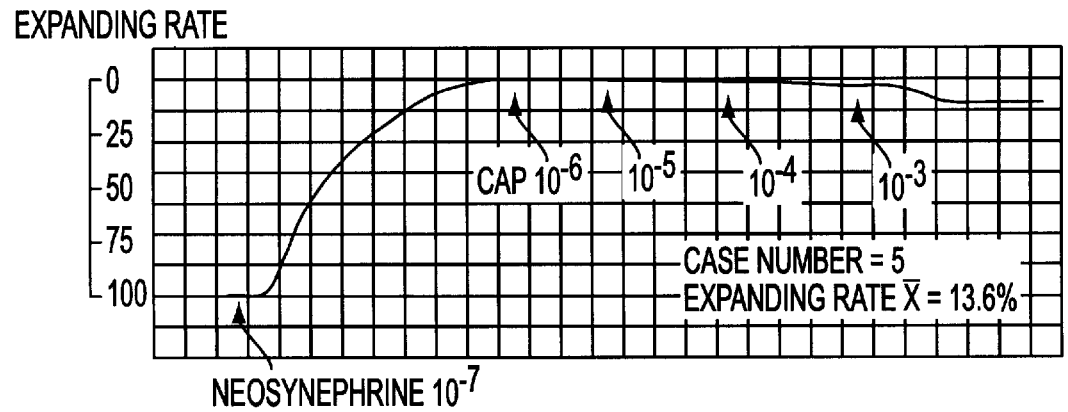
FIG. 3d shows the relationship between vasodilation capability and dose/concentration of Capoten as the control group when endothelium is removed.

The isolated perfusion test of the vascular circle proved that the composition had effect of expanding arteries. This effect was endothelium-dependent and dose-dependent. With the endothelium, the higher the dose of the composition, the stronger the effect of expanding the blood vessel. The maximal expanding rate was up to 96% (see FIG. 4).

9. The clinical test for the composition to lower blood pressure.

9.1. Materials and Methods:

Observed subjects: 44 patients with essential hypertension. All of them were adults aged below 60, their average age was 53±12.7. All of them were diagnosed as hypertension according to the diagnostic standard of WHO. Selected another 44 patients with essential hypertension at random as the control group. The patients of the control group were treated with Captopril. The patients of the control group were adults aged below 59, and their average age was 47±7.8. The sex and the course of disease of these two groups were listed in table 13. The patients stopped taking hypotensor a week before taking part in the test. Treatment method: gave the patients of the treatment group 1.5 g composition each time, 3 times a day, and 5 days in all. If the blood pressure was not reduced to the normal scope, then a dose (0.5 g) was increased every 5 days. The crescendo every 5 days, and the maximal dose couldn't exceed 3 g each time and 3 times a day. The whole course of treatment was 20 days. 25 mg Captopril was given to the patients of the control group each time and three times a day. If the blood pressure was not reduced to the normal scope, then a dose (12.5 mg) was increased every 5 days. The crescendo every 5 days, and the maximal dose couldn't exceed 75 mg each time and three times a day. The whole course of treatment was 20 days too.

The blood pressure before treatment: All the patients stopped taking hypotensor a week before treatment. Then the blood pressure was measured once a day continuously for 5 days. Took the mean of the 5 values (non same day) as the blood pressure before treatment.

The blood pressure after treatment: Measured the blood pressure once a day after the treatment. Took the mean of the 5 values measured on the 16th, 17th, 18th, 19th, 20th day after the treatment as the blood pressure after the treatment. Examined the blood routine, the urine routine, the functions of liver, the renal function, the serum electrolyte (including $K^+$, $Na^+$, $Cl^-$), the blood-lipid, the blood sugar, the ECG of every day before and after the treatment.

The criteria of therapeutic effect:

Obvious effectiveness: The diastolic pressure was reduced more than 1.33 kpa and become normal or it was reduced more than 2.67 kpa after treatment.

Effectiveness: The diastolic pressure was reduced of less than 1.33 kpa but it became normal, or it was reduced of 1.33–2.53 kpa. As to the systolic hypertension, the systolic pressure was reduced more than 4 kpa. Ineffectiveness: The decrement of the blood pressure after the treatment didn't achieve the above standard.

2. Results:

Analysis of the therapeutic effect: The blood pressures and the decrements before and after the treatment were compared and listed in Table 14. Both of the groups had very significant difference (P<0.01) by T test with own control. But no significant difference exited between the two groups (P>0.05). Moreover, there was not significant difference between the effects of decreasing the blood pressure of the two groups after the treatment (see table 14).

The changes of ECG and blood biochemistry before and after the treatment: Before the treatment, there were 10 cases with ventricular premature beats, & cases with atrial premature beats, 4 cases with absolute left bundle branch block, 7 cases with absolute right bundle branch block, 10 cases with left ventricular hypertrophy, 16 cases with ischemic like changes on ST-T segment of lead II, III, avF, $V_4$–$V_6$. The total of the patient foe two groups was 88. After the treatment, improved ST-T segment of lead $V_4$–$V_6$ was showed in the ECG of 12 patients, the atrial premature beats of 8 patients and the ventricular premature beats of 7 patients disappeared, and no obvious difference was showed in blood electrolyte ($K^+$, $Na^+$, $Cl^-$) and blood sugar.

3. Conclusion:

The composition could lower the essential hypertension and the renal hypertension significantly. The effect of lowing blood pressure appeared at 30 minutes after the administration and reached the peak at 2 hours after the administration. The effect would last for more than 3 hours and was dose-dependent. The blood pressure would remain normal for 20 hours after the drug withdrawn. It could lower the levels of blood-lipid concurrently. Therefore the composition was especially suitable for those with hypertension accompanied by hyperlipidemia. No adverse effect was observed among the 44 patients treated with the composition. The total effective rate was 77% (see table 15).

The clinical test of the formulation which consists of the extract of pine needle of the invention, the extract of Radix Puerariae, the pearl stratum power (refers to: "formulation" hereafter) will be disclosed as follows:

10. The observation of the therapeutic effect for the formulation to treat myocarditis Subjects and Methods:

1. Treatment group: 11 patients with viral myocarditis and 5 patients with rheumatic myocarditis were selected as the treatment group (16 cases in all) according to the diagnostic criteria of myocarditis, including 9 male and 7 female aged 6–17, whose average age was 11.6±2.8, 10 cases with the ECG of showed myocardial ischemia, 9 cases with arrhythemia (wherein 6 cases with tachycardia, 4 cases with frequent premature beats, and 2 cases with bradycardia).
2. Control group: 12 patients were selected as the control group, including 8 cases with viral myocarditis, 4 cases with rheumatic myocarditis. There were 5 male cases and 7 female cases aged between 4 and 17, their average age was 9.1±2.6. The ECG of 9 cases showed myocardial ischemia, 7 cases showed arrhythemia (wherein 5 cases with tachycardia accompanied by frequent premature beats, and 2 cases with bradycardia).
3. Took blood from the fasting patients after the treatment: ESR, GOT, CPK, CPK-MB, ECG and RF (rheumatoid factor) were examined.
4. 1.5 g of the formulation was given to the patients of the treatment group each time, three times a day. In the control group, the conventional method was used: 10% Glucose solution 500 ml+Vit C 3.0 g+ATP 40 mg+coenzyme 100 u were administrated by intravenous drip once a day, and coenzyme $Q_{10}$ by muscular injection once a day, 30 days a course of treatment. The patients with rheumatic myocarditis in the two groups were reviewed conventional antirheumatics treatment.

The criteria for therapeutic effect and the statistical treatment Remarkable effectiveness: all of the indexes including ESR, GOT, CPK, CPK-MB, ECG, RF and so on restore normal.

Effectiveness: the above indexes were obviously improved after the treatment, but didn't restore normal (ECG still showed abnormality of heat rate, frequent premature heats or slight changes of ST-T segments).

Ineffectiveness: the above indexes were improved to some degree, but still remained obviously abnormal.

T-test for significance was used.

Results: The comparison of the therapeutic effects between the two groups was showed as follows (see table 16).

11. The therapeutic effect analysis for the formulation to treat hyperlipidemia:

The patients with hyperlipidemia but without diabetes and liver diseases or renal diseases were selected as the observed subjects. During the observation, all of the patients stopped taking the medicines had effects on the lipid metabolism but still kept the diet as usual.

11.1 Clinical data: 110 cases were divided into the treatment group with 70 cases and the control group with 40 cases. There were 50 male cases and 20 female cases aged between 40 and 67 in the treatment group, and their average age was 55. There were 41 cases with hypercholesterolemia (TC) and 55 cases with hypertriglyceridemia (TG). In the control group, there were 28 male cases and 12 female cases (total 40 cases) aged between 40–66 and their average age was 54, including: 30 cases with hypercholesterolemia and 30 cases with hypertriglycoridemia. The two groups were comparable in sex, age and symptom.

11.2 Groups and therapeutic method 11.2.1 The treatment group: the formulation 1.5 g each time, three times a day, once a month a course of treatment.

11.2.2. The control group: the soft capsule of erythrinus eveningprimrose root oil, 2 capsules each time, three times a day (Notice: 0.5 g each capsule, the drug was produced at the sixth pharmaceutical factory of Wuxi), one month a course of treatment.

11.2.3. Observation method: blood routine, urine routine, liver function, renal function especially the blood lipid and ECG of all the patients were examined before and after the treatment.

11.3. Results:

11.3.1. The therapeutic effect on hypercholesterolmia (TC):

Among the 41 cases in the treatment group:

Remarkable effectiveness: 20 cases,

Effectiveness: 16 cases,

Ineffectiveness: 5 cases.

The total effective rate: 87.8%;

Among the 30 cases in the control group;

Remarkable effectiveness: 4 cases,

Effectiveness: 8 cases,

Ineffectiveness: 18 cases,

The total effectiveness rate: 40%.

There is significant difference between the two groups ($X^2$=18.16 P<0.01). The difference of TC before and after the treatment were 2.46±0.69 mmol/L in the treatment group and 0.84±0.33 mmol/L in the control group, respectively. The effect of lowering TC in the treatment group was much stronger than that in the control group (t=11.86 P=0.001). In the treatment group, if TC before treatment was compared with that after treatment, then t=22.829 P<0.001, which showed the effect of lowering TC in the treatment group was reliable.

11.3.2. The therapeutic effect of hypertriglydemia (TG):

Among the 55 cases in the treatment group:

Remarkable effectiveness: 24 cases,

Effectiveness: 25 cases,

Ineffectiveness: 6 cases,

The total effective rate: 89.1%,

Among the 30 cases in the control group;

Remarkable effectiveness: 9 cases,

Effectiveness: 5 cases,

Ineffectiveness: 16 cases,

The total effective rate: 46.67%.

There is significant difference between the two groups ($X^2$=18.04, P<0.01). The difference of TG before and after the treatment were 1.57±0.52 mmol/L in the treatment group and 1.01±0.31 mmol/L in the control group, respectively. The effect of lowering TG in the treatment group was much stronger than that in the control group (t=5.385 P=0.001). In the treatment group, if TC before treatment was compared with that after treatment, then t=22.391 P<0.001, which showed the effect of lowering the TG in the treatment group was reliable.

No adverse effect was found during the treatment by the formulation. Furthermore, there was no obvious change of blood routine, urine routine, liver function, renal function and ECG before and after the treatment.

11.3.3. Conclusion:

The total effective rates for the formulation to treat hypercholesterolemia and hypertriglyceridemia were 87.8% and 89.1%, respectively, which significant difference existed comparing with that in the control group. These proved that the effect for the formulation to treat hyperlipeasa was much better than that of the control drug and had reliable effect of decreasing the TC and TG. If compared the effect of the formulation with that of the control drug by statistical treatment, then P<0.001. This proved that its effect to lower blood lipid was super to the control drug.

12. The clinical test of the formulation to treat carliovascular disease 12.1. Subjects and Materials:

12.1.1. Subjects: According to the diagnostic standard of WHO, the patients with essential hypertension, angina pectoris resulted from CHD, hyperlipemia accompanied by high blood viscosity were selected as the observed subjects, which were divided into three groups.

12.1.1.1. Group of hypertension: Total 62 cases, male: 37 cases, female: 25 cases. The ages were between 27–74. The average age was 52.3±26.5. Their medical histories lasted 2.9±3.12 years on average. Primary hypertension: 18 cases (29%), Secondary hypertension: 40 cases (64.5%), Tertiary hypertension: 4 cases (6.5%).

12.1.1.2. Group of angina pectoris: total 40 cases, male: 21 cases, female: 19 cases. The age was between 45–79. The average age was 59.8±15.2. Stable labor angina pectoris: 26 cases (65%), Unstable angina pectoris: 14 cases (35%).

12.1.1.3. Group of hyperlipemia and hyperviscosity: total 65 cases, male: 42 cases, female: 18 cases. The average age was 55.3±5.0.

12.1.2 Methods:

12.1.2.1. The therapeutic method: The patients stopped taking hypotensor, anti-angina agent and antilipemic agent, and took 1–1.5 g of the formulation each time, three times a day, 4–6 weeks a course of treatment. The patients accompanied left ventricular hypertrophy were combined with Enalapril maleate, the patients attacked by angina pectoris were administered the nitrates or Suxiaojiuxingwan, while kept the other conventional treatment unchanged.

12.2. Results 12.2.1 Group of hypertension: See table 17, 18 for the changes of systolic blood pressure (SBP) and diastolic blood pressure (DBP) before and after the treatment.

12.2.2. Group of angina pectoris: See table 19, 20 for the therapeutic effect on symptoms, ECG and various angina 12.2.3. Group of hyperlipemia accompanied hyperviscosity: see table 21 for the changes of blood-lipid and hemorheology before and after the treatment.

12.3. Discussion:

The clinical therapeutic effect for the formulation to treat hypertension, CHD, angine pectoris, and hyperlipemia accompanied by high blood viscosity was satisfactory. The SBP and DBP were reduced by 23.4% and 20.5%, respectively. The total effective rate was 96.8%. The effective rates for the improvement of symptom and ECG of the patients with angina were 95% and 65% respectively. The effective rates of stable labor angina and unstable angina were 100% and 85.7%, respectively. The levels of CH, TG, LDL-C were reduced by 18.0%, 27.2%, 39.2%, respectively, however, the level of HDL-C was increased by 58.8%. Hematocrit, whole blood specific viscosity and plasma specific viscosity were reduced by 27.1%, 16.6% and 24.6%, respectively. There are significant or very significant difference (P<0.05 or 0.01) in all kind of the above indexes between before and after the treatment. This proved that the formulation could lower the levels of blood pressure, cholesterol, triglyceride, LDL-C, hematocrit, whole blood specific visocsity and plasma specific viscosity while increase that of HDL-C, protect the heart and relieve angina etc.

TABLE 1

Acute Effect for the Extract of Pine Needle to Lower Blood Pressure of Rats with Hypertension (mean artery pressure MAD ± SD) mmHg

| Group | n | before drug given MAP | 30 min after drug given MAP | descending rate % | 1 hour after drug given MAP | descending rate % | 2 hour after drug given MAP | descending rate % | 3 hour after drug given MAP | descending rate % |
|---|---|---|---|---|---|---|---|---|---|---|
| ① normal control | 10 | 111.8 ± 1.73 | 106.2 ± 1.09 | 5.0 ± 0.48 | 119.7 ± 1.16 | 1.0 ± 0.08 | 110.0 ± 1.42 | 0.8 ± 0.02 | 111.5 ± 1.33 | 0.3 ± 0.01 |
| ② blank control | 10 | 202.58 ± 3.86 | 203.6 ± 3.77 | −0.5 ± 0.06 | 204.3 ± 3.81 | −0.9 ± 0.05 | 203.9 ± 4.12 | −0.7 ± 0.04 | 203.1 ± 3.79 | −0.3 ± 0.02 |
| ③ group given with Folium Apocyni Veneti | 10 | 198.7 ± 4.33 | 192.3 ± 4.67 | 3.2 ± 0.62 | 186.4* ± 4.08 | 6.2* ± 0.81 | 186.4* ± 4.33 | 8.1* ± 1.22 | 188.1 ± 4.29 | 5.8 ± 0.92 |
| ④ low dose group with renal hypertension SP | 10 | 1.64.7 ± 3.24 | 154.3* ± 3.06 | 6.8* ± 1.13 | 146.2** ± 3.72 | 11.2** ± 2.11 | 141.1** ± 4.10 | 14.3** ± 2.82 | 146.7** ± 3.76 | 10.9** ± 1.71 |
| | 10 | 201.6 ± 3.41 | 186.0* ± 4.03 1.41 | 7.6* ± 3.77 | 174.6** ± 1.76 | 13.4** ± 3.23 | 170.1** ± 2.17 | 15.6** ± 4.06 | 178.4** ± 1.30 | 11.5** ± |
| ⑤ high dose group with renal hypertension SP | 10 | 172.3 ± 4.68 | 156.4 ± 3.09 | 9.2* ± 1.66 | 146.7** ± 4.02 | 14.9** ± 1.82 | 140.2** ± 3.92 | 18.6** ± 2.07 | 148.7** ± 3.71 | 18.7** ± 2.01 |
| | 10 | 206.5 ± 4.02 | 182.2** ± 3.62 | 11.8** ± 1.73 | 174.1** ± 4.01 | 15.7** ± 1.96 | 170.2** ± 3.75 | 17.6** ± 1.98 | 176.3** ± 4.15 | 14.6 ± 2.10 |

*P < 0.05
**P < 0.01

TABLE 2

Long-term decreasing blood pressure effect of the extract of pine needles on SP rats

| Group | n | blood pressure before treatment ± SD mmHg | Blood pressure after treatment ± SD mmHg | decreasing rate ± SD % | Arterial blood pressure after treatment ± SD mmHg | mean arterial blood pressure after treatment ± SD mmHg |
|---|---|---|---|---|---|---|
| ① normal control | 10 | 102.4 ± 2.38 | 108.0 ± 2.41 | −0.6 ± 1.22 | 120.6/92.4 ±3.02/±1.0 | 101.8 ± 2.04 |
| ② blank control group | 10 | 188.8 ± 5.85 | 189.6 ± 6.68 | −0.4 ± 1.19 | 216.8/176.2 ±6.16/±6.47 | 180.5 ± 6.08 |
| ③ Folium pocyni Veneti group | 10 | 192.0 ± 2.28 | 170.0 ± 4.1 | 11.52* ± 1.26 | 202.2/160.0 ±5.99/±4.2 | 174.1* ± 4.73 |
| ④ low dose group | 10 | 188.7 35 3.88 | 130.8*** ± 2.58 | 30.7*** ± 0.93 | 160.4/126.6 ±3.19/±2.79 | 187.6*** ± 2.79 |
| ⑤ moderate dose group | 10 | 197.6 ± 5.91 | 120.0*** ± 4.47 | 38.83*** ± 3.68 | 150.0/119.8 ±3.99/±1.20 | 128.9*** ± 1.93 |
| ⑥ high dose group | 10 | 194.0 ± 2.28 | 102.4*** ± 4.58 | 47.22 ± 1.16 | 128.7/96.8 ±5.01/±3.11 | 107.4*** ± 4.75 |

*$P < 0.05$
***$P < 0.001$

TABLE 3

The therapeutic effect of the extract from pine needle on patients with hypertension

| Groups | Case numbers | age | blood pressure before treatment | blood pressure after treatment | Remarkable effective rate % | effective rate % |
|---|---|---|---|---|---|---|
| treatment group | 85 | 52.4 ± 5.62 | 186.1/118.1 ±3.82/±3.82 | 136.3**/90.1*** ±4.06/±3.11 | 53.44*** | 86.36* |
| control group | 56 | 51.1 ± 6.33 | 178.8/114.8 ±5.64/±3.61 | 162.37*/106.3* ±5.42/4.06 | 24.69 | 67.38 |

*$P < 0.05$
**$P < 0.01$
***$P < 0.001$

TABLE 4

The effect of the extract from pine needle on the blood-lipid of the animals with hyperlipemia ($\overline{X} \pm SD$)

| Group | total cholesterol | | | | triglyceride | | | |
|---|---|---|---|---|---|---|---|---|
| | before HFD | after HFD | After treatment | DR % | before HFD | after HFD | after treatment | DR % |
| 1) blank control group n = 7 | 1.37 ± 0.098 | 28.89 ± 1.44 | 25.24 ± 1.64 | 4.77 ± 8.39 | 1.16 ± 0.05 | 2.06 ± 0.17 | 1.71 ± 0.14 | 17.30 ± 1.37 |
| 2) positive control group n = 10 | 1.29 ± 0.13 | 26.67 ± 1.57 | 19.48* ± 0.88 | 28.20 ± 4.27 | 1.07 ± 0.07 | 1.87 ± 0.90 | 1.64** ± 0.11 | 16.03 ± 2.76 |
| 3) low dose group n = 10 | 1.42 ± 0.12 | 27.36 ± 1.60 | 15.46 ± 1.60 | 43.49*** ± 5.34 | 1.15 ± 0.11 | 2.03 ± 0.16 | 1.26 ± 0.18 | 37.93 ± 10.61 |
| 4) prevention group n = 10 | 1.38 ± 0.11 | 17.62*** ± 1.56 | 8.23*** ± 1.55 | 53.29*** ± 6.12 | 1.08 ± 0.06 | 1.28 ± 0.07 | 1.01 ± 0.04 | 21.09** ± 7.32 |
| 5) high dose group n = 10 | 1.52 ± 0.09 | 29.75 ± 0.96 | 12.61 ± 1.84 | 57.61 ± 4.98 | 0.98 ± 0.10 | 2.25 ± 0.19 | 1.16*** ± 0.06 | 48.44*** ± 9.07 |
| | | <1> | <2> | <3> | | <4> | <5> | <6> |

| Group | high density lipoprotein | | | | low density lipoprotein | | | |
|---|---|---|---|---|---|---|---|---|
| | before HFD | after HFD | After treatment | IR % | before HFD | after HFD | after treatment | DR % |
| 1) blank control group n = 7 | 0.56 ± 0.05 | 0.79 ± 0.08 | 0.68 ± 0.03 | −11.64 ± 6.53 | 0.91 ± 0.11 | 8.90 ± 0.49 | 8.22 ± 0.88 | 8.78 ± 4.06 |
| 2) positive control group n = 10 | 0.65 ± 0.09 | 0.83 ± 0.06 | 0.74 ± 0.05 | 8.90 ± 3.71 | 1.21 ± 0.25 | 9.20 ± 0.42 | 5.71* ± 0.37 | 37.38* ± 5.33 |
| 3) low dose group n = 10 | 0.62 ± 0.03 | 0.89 ± 0.11 | 1.02 ± 0.10 | 12.74 ± 9.75 | 0.96 ± 0.09 | 9.31 ± 0.44 | 4.75** ± 0.52 | 48.97*** ± 5.46 |

TABLE 4-continued

The effect of the extract from pine needle on the blood-lipid of the animals with hyperlipemia ($\overline{X} \pm SD$)

| | | | | | | | | |
|---|---|---|---|---|---|---|---|---|
| 4) prevention group n = 10 | 0.59 ± 0.05 | 0.72 ± 0.09 | 1.41*** ± 0.18 | 48.93*** ± 12.40 | 1.11 ± 0.05 | 5.02 ± 0.61 | 3.09** ± 0.24 | 38.45*** ± 4.58 |
| 5) high dose group n = 10 | 0.65 ± 0.06 | 0.77 ± 0.12 | 1.36*** ± 0.22 | 43.38** ± 11.04 | 1.07 ± 0.07 | 9.42 ± 0.50 | 3.03*** ± 0.45 | 67.83*** ± 7.11 |
| | | <7> | <8> | <9> | | <10> | <11> | <12> |

(Note: HFD = high fat diet; DR = decreasing rate; IR = increasing rate)
*$P < 0.05$
***$P < 0.001$ <1> Significant difference existed between Group 4 and Groups 1, 2, 3 and 5. <2> Significant difference existed between Group 4 and the other groups, and between Group 1 and the other groups. <3> Significant difference existed between Group 4 and Groups 1, 2 and 3, between Group 5 and Groups 1 and 2, and between Group 1 and Groups 2 and 3. <4> Significant difference existed between Group 4 and the other groups. <5> Significant difference existed between Group 1 and Groups 3, 4 and 5, and between Group 2 and Groups 1, 4 and 5. <6> Significant difference existed between Group 5 and the other groups, and between Group 3 and Groups 1, 2 and 4. <7> Significant difference existed between Group 5 and the other groups, and between Group 3 and Groups 1, 2 and 4. <8> Significant difference existed between Group 5 and Groups 1 and 2, and between Group 4 and Groups 1 and 2. <9> Significant difference existed between Group 5 and Group 1. <10> Significant difference existed between Group 4 and the other groups. <11> Significant difference existed between Group 1 and the other groups, and between Group 2 and Groups 4 and 5. <12> Significant difference existed between Group 1 and the other groups, between Group 5 and Group 2 and 4, and between Groups 3 and 4.

TABLE 5

The effect of the extract from pine needle on the PTH and CT of rats

| | | PTH $\overline{X} \pm SD$ | | | CT $\overline{X} \pm SD$ | | |
|---|---|---|---|---|---|---|---|
| Groups | N | before treatment | after treatment | decreasing rate % | after treatment | after treatment | decreasing rate % |
| (1) normal control group | 5 | 0.34 ± 0.03 | 0.33 ± 0.04 | 2.94 ± 0.12 | 186.5 ± 7.69 | 184.33 ± 8.25 | −1.03 ± 0.05 |
| (2) blank control group | 5 | 0.88 ± 0.14 | 0.95 ± 0.12 | −7.95 ± 0.36 | 119.50 ± 7.56 | 111.25 ± 13.72 | −6.90 ± 1.22 |
| (3) SP treatment group | 5 | 0.97 ± 0.13 | 0.82 ± 0.16 | 15.46 ± 2.51 | 112.10 ± 8.06 | 136.52 ± 13.44 | 21.78 ± 2.96 |
| P value | | <0.001 Difference existed between Group 1 and Groups 2 and 3. | <0.05 Difference existed between Group 1 and Groups 2 and 3. | <0.05 Difference existed between Group 3 and Groups 1 and 2. | <0.001 Difference existed between Group 1 and Groups 2 and 3. | <0.05 Difference existed between Group 1 and Groups 2 and 3. | <0.001 Difference existed between Group 3 and Groups 1 and 2. |

TABLE 6

The test for inhibiting platelet aggregation in vitro

| | | 1′ aggregation rate % (ngEq/ml) | | Maximal aggregation rate (Amas)pg/ml | |
|---|---|---|---|---|---|
| Groups | n | $\overline{X} \pm SD$ | rate of aggregation-inhibition % | $\overline{X} \pm SD$ | Rate of aggregation-inhibition % |
| (1) ADP + phosphate buffer | 5 | 27.16 ± 5.29 | | 42.34 ± 2.46 | |
| (2) ADP + Danshen | 5 | 17.47* ± 2.9 | 35.68 | 26.56* ± 3.25 | 38.0 |
| (3) ADP + Radix Puerariae | 5 | 12.05* ± 2.0 | 55.63 | 22.14* ± 2.74 | 48.32 |
| (4) ADP + pine needle | 5 | 6.91** ± 1.20 | 74.56*** | 15.63* ± 2.91 | 63.52** |

TABLE 6-continued

The test for inhibiting platelet aggregation in vitro

| Groups | n | 1' aggregation rate % (ngEq/ml) | | Maximal aggregation rate (Amas)pg/ml | |
|---|---|---|---|---|---|
| | | $\overline{X} \pm SD$ | rate of aggregation-inhibition % | $\overline{X} \pm SD$ | Rate of aggregation-inhibition % |
| ⑤ ADP + compound | 5 | 5.27** ± 1.13 | 80.60*** | 14.13* ± 2.34 | 67.02 |
| P value | | <0.001 | | <0.001 | |
| | | Difference existed between Group 1 and the other groups. | | Difference existed between Group 1 and the other groups. | |
| | | Difference existed between Group 2 and Groups 4 and 5. | | Difference existed between Group 2 and Groups 4 and 5. | |
| | | | | Difference existed between Group 3 and Groups 4 and 5. | |

*$P < 0.05$
**$P < 0.01$
***$P < 0.001$

TABLE 7

The effect of the extract from pine needle on the hemorheology of the patients with hyperviscosity.

| Groups | n | age | ESR | | Haematocrit | |
|---|---|---|---|---|---|---|
| | | | before treatment | after treatment | before treatment | after treatment |
| Treatment group | 87 | 55.3 ± 4.2 | 28.3 ± 3.42 | 15.23 ± 2.61 | 52.83 ± 1.10 | 45.02** ± 1.00 |
| Control group | 44 | 54.6 ± 5.6 | 26.7 ± 4.12 | 20.2* ± 3.88 | 51.16 ± 1.22 | 49.67 ± 1.03 |

| Groups | Specific viscosity of plasma | | Specific viscosity of whole blood | | | |
|---|---|---|---|---|---|---|
| | | | High shear | | Low shear | |
| | before treatment | after treatment | before treatment | after treatment | before treatment | after treatment |
| Treatment group | 2.02 ± 0.10 | 1.72** ± 0.16 | 6.79 ± 0.18 | 5.88** ± 0.17 | 12.33 ± 0.32 | 7.80** ± 0.50 |
| Control group | 1.97 ± 0.12 | 1.84 ± 0.06 | 6.81 ± 0.17 | 6.44** ± 0.18 | 11.89 ± 0.57 | 9.62** ± 0.98 |

*$P < 0.05$
**$P < 0.01$
***$P < 0.001$

TABLE 8

The effect of the extract from pine needle on the platelet aggregation rate of the patients with hyperaggregation ($\overline{X} \pm SD$)

| Groups | n | 1' aggregation rate % | | | maximal aggregation rate % | | |
|---|---|---|---|---|---|---|---|
| | | before treatment | after treatment | inhibition rate % | before treatment | after treatment | Inhibition rate % |
| treatment group | 68 | 56.33 ± 7.33 | 21.71*** ± 3.56 | 61.46*** ± 4.65 | 87.45 ± 11.32 | 44.37*** ± 10.16 | 49.26*** ± 9.64 |
| control group | 35 | 52.65 ± 6.46 | 48.88 ± 4.87 | 7.5 ± 1.23 | 88.06 ± 10.25 | 80.12* ± 12.76 | 9.02* ± 3.23 |

*$P < 0.05$
***$P < 0.001$

TABLE 9

The effect of the extract from pine needle on heart rate, $TXB_2$, $PGI_2$ of the patients with CHD.

| Groups | n | heart rate before treatment | heart rate after treatment | $TXB_2$ before treatment | $TXB_2$ after treatment | $PGI_2$ before treatment | $PGI_2$ after treatment | $TXB_2/PGI_2$ before treatment | $TXB_2/PGI_2$ after treatment |
|---|---|---|---|---|---|---|---|---|---|
| Treatment group | 42 | 86.44 ± 10.62 | 74.32 ± 7.36 | 163.12 ± 81.23 | 136.27** ± 74.36 | 36.23 ± 14.60 | 157.96*** ± 92.65 | 4.50 ± 2.06 | 0.86*** ± 0.47 |
| control group | 25 | 87.6 ± 11.24 | 86.28 ± 10.50 | 156.18 ± 83.26 | 153.06 ± 81.54 | 38.57 ± 15.08 | 55.38* ± 15.67 | 4.05 ± 2.13 | 2.76* ± 0.87 |

*$P < 0.05$
**$P < 0.01$
***$P < 0.001$

TABLE 10

The effect of the extract from pine needle on blood-lipid of the patients with CHD.

| Groups | n | total cholesterol before treatment | total cholesterol after treatment | triglyceride before treatment | triglyceride after treatment | high density lipoprotein before treatment | high density lipoprotein after treatment |
|---|---|---|---|---|---|---|---|
| treatment group | 42 | 6.96 ± 1.06 | 4.82*** ± 0.92 | 2.10 ± 0.82 | 1.63* ± 0.66 | 1.16 ± 0.30 | 1.43 ± 0.32 |
| control group | 25 | 6.04 ± 1.13 | 5.89 ± 1.02 | 1.98 ± 0.76 | 1.84 ± 0.81 | 1.21 ± 0.36 | 1.24 ± 0.33 |

*$P < 0.05$
***$P < 0.001$

TABLE 11

The effect of the extract from pine needle on ECG of the patients with CHD

| Groups | n | abnormal ECG | remarkable effectiveness case number | remarkable effectiveness % | improvement case number | improvement % | total effective rate case number | total effective rate % |
|---|---|---|---|---|---|---|---|---|
| treatment groups | 42 | 38 | 8 | 21.1 | 6 | 42.1 | 24 | 63.2 |
| control group | 25 | 21 | 2 | 9.5 | 3 | 14.3 | 5 | 23.8 |

TABLE 12

The effect of the extract from pine needle on Serum $SOD_1$ and Serum lipid peroxide of the senile patients

| | $SOD_1$ (ug/l) | lipid peroxide |
|---|---|---|
| before administration | 12436 ± 0.24.71 | 9.62 ± 3.40 |
| one month after administration | 1162.06 ± 432.64* | 7.36 ± 2.58* |
| three months after administration | 411.05 ± 274.38*** | 5.62 ± 2.13** |

*$P < 0.05$
**$P < 0.01$
***$P < 0.001$

TABLE 13

Comparison of the general condition of patients between the 2 groups

| Groups | sex male | sex female | years old age | years old $\bar{X} \pm SD$ | course of disease (year) <5 | course of disease (year) 5–10 | course of disease (year) >10 |
|---|---|---|---|---|---|---|---|
| Composition | 20 | 24 | 43–66 | 53 ± 12.7 | 24 | 12 | 8 |
| Captopril | 28 | 16 | 39–59 | 47 ± 7.8 | 24 | 12 | 8 |

TABLE 14

Comparison the decrements of blood pressure (Kpa) before and after treatment ($\overline{X} \pm SD$)

| Groups | case number | systolic pressure | | | diastolic pressure | | |
|---|---|---|---|---|---|---|---|
| | | before treatment | after treatment | decrement | before treatment | after treatment | decrement |
| composition | 41 | 26.3 ± 3.2 | 18.9 ± 3.8 | 7.4 ± 2.9* | 16.1 ± 2.1 | 11.9 ± 3.9 | 4.2 ± 1.9* |
| captopril | 44 | 23.7 ± 5.3 | 17.1 ± 2.6 | 6.6 ± 0.7* | 14.9 ± 2.9 | 10.6 ± 2.2 | 4 ± 2.8* |

*$P < 0.01$ (comparison within the group) (Comparison between the 2 groups) $P < 0.05$

TABLE 15

Comparison of the effects of decreasing the blood pressure before and after treatment between the 2 groups

| Groups | case number | remarkable effectiveness | Effectiveness | ineffectiveness | total effective rate (%) |
|---|---|---|---|---|---|
| composition | 44 | 24 | 10 | 10 | 77 |
| captopril | 44 | 26 | 10 | 8 | 82 |

$P > 0.05$ (Comparison between the 2 groups)

TABLE 16

| | case number | ECG case number (%) | | | serum enzyme case number (%) | | | ESR case number (%) | | |
|---|---|---|---|---|---|---|---|---|---|---|
| | | remarkable effectiveness | effectiveness | ineffectiveness | remarkable effectiveness | effectiveness | ineffectiveness | remarkable effectiveness | effectiveness | ineffectiveness |
| treatment group | 16 | 10*** (63) | 5* (41) | 1* (6) | 12*** (75) | 4 (25) | 0 | 9*** (56) | 6* (38) | 1* (6) |
| control group | 12 | 5 (41) | 4 (33) | 3 (26) | 8 (67) | 3 (25) | 1 (8) | 5 (41) | 5 (41) | 2 (18) |

*$P < 0.05$,
**$P < 0.01$,
***$P < 0.001$

TABLE 17

The therapeutic effect for the formulation to lower blood pressure.

| | SBP Kpa (mmHg) | DBP Kpa (mmHg) |
|---|---|---|
| before treatment | 24.4 ± 9.7 (183 ± 72.9) | 14.8 ± 0.9 (110.6 ± 6.6) |
| after treatment | 18.7 ± 3.9 (140.3 ± 29.0) | 11.6 ± (86.6 ± 11.9) |
| Decrement | 5.7 (42.8) | 3.2 (23.8) |
| Decreasing rate (%) | 23.4 | 20.5 |
| P | <0.01 | <0.01 |

TABLE 18

The therapeutic effect of the formulation on hypertension in different periods

| | case number of remarkable effectiveness | case number of effective (%) | | total case number of effectiveness (%) | | case number of ineffectiveness (%) | |
|---|---|---|---|---|---|---|---|
| Primary | 18 | 100.0 | | 18 | 100.0 | | |
| Secondary | 36 | 90.0 | 4 | 10.0 | 40 | 100.0 | |
| Tertiary | 2 | 50.0 | | | 2 | 50.0 | 2 | 50.0 |
| Total | 56 | 90.3 | 4 | 6.5 | 60 | 96.8 | 2 | 3.2 |

TABLE 19

The therapeutic effect of the formulation on the symptoms and ECG of the patients with angina (n = 40)

|  | remarkable effectiveness case number % | Effectiveness case number % | total effectiveness case number % | ineffectiveness case number % |
|---|---|---|---|---|
| therapeutic effect on symptom | 20  50.0 | 18  15.0 | 38  95.0 | 2  5.0 |
| therapeutic effect on ECG | 10  25.0 | 16  40.0 | 26  65.0 | 14  35.0 |

TABLE 20

The therapeutic effect of the formulation on various angina (n = 40)

| The type of angina | case number | remarkable effectiveness case number % | effectiveness case number % | total effectiveness case number % | ineffectiveness case number % |
|---|---|---|---|---|---|
| stable labor pectoris | 26 | 12  46.2 | 14  53.9 | 26  100.0 |  |
| unstable labor pectoris | 14 | 8  57.1 | 4  28.6 | 12  85.7 | 2  4.3 |
| in total | 40 | 20  50.0 | 18  45.0 | 38  95.0 | 2  5.0 |

TABLE 21

The effect of the formulation on blood-lipid and hemorheology (n = 65)

|  | CH (mmol/L) | TG | HDL-Ch | LDL-Ch % | hematocrit | Whole blood specific viscosity (high shear) | plasma specific viscosity (CP) |
|---|---|---|---|---|---|---|---|
| before treatment | 6.4 ± 8.2 | 1.8 ± 1.5 | 1.0 ± 0.2 | 3.6 ± 1.3 | 50 ± 0.4 | 4.95 ± 1.15 | 1.63 ± 0.53 |
| after treatment | 5.3 ± 0.6 | 1.3 ± 0.2 | 1.5 ± 1.1 | 2.6 ± 0.5 | 45 ± 0.5 | 4.13 ± 1.14 | 1.22 ± 0.16 |
| ↑ or ↓ | 1.1↓ | 0.5↓ | 0.5↓ | 1.0↑ | 5↓ | 0.82↓ | 0.41↓ |
| ↑ or ↓ (%) | 18.0↓ | 27.2↓ | 58.8↓ | 39.2↓ | 10.0↓ | 16.6↓ | 24.6↓ |
| P | <0.05 | <0.01 | <0.01 | <0.01 | <0.001 | <0.01 | <0.01 |

What is claimed is:

1. A pine needle extract, wherein the extract is from pine needles of *Pinus tabulaeformis* Carr, *Pinus massoniana* Lamb or *Pinus yunnanensis* Franch, is brown in solid state, is water-soluble and has a maximum absorption peak at about 242 nm in the ultraviolet-visible light spectrum.

2. The extract of claim 1, further comprising an extract of Radix Puerariae and pearl stratum powder.

3. The extract of claim 1, further comprising an extract of Radix Puerariae, wherein the proportion of pine needle extract and Radix Puerariae extract is from 3:1 to 5:2.

4. The extract of claim 1, further comprising pearl stratum powder, wherein the proportion of pine needle extract and pearl stratum powder is from 20:1 to 2:1.

5. The pine needle extract according to claim 1, wherein the extract is from pine needles of Pinus tabulaeformis Carr.

6. The pine needle extract according to claim 1, wherein the extract is from pine needles of Pinus massoniana Lamb.

7. The pine needle extract according to claim 1, wherein the extract is from pine needles of Pinus yunnanensis Franch.

8. A therapeutic composition comprising an effective amount of the extract of claim 1 and a pharmacologically acceptable carrier or excipient.

9. The therapeutic composition of claim 8 further comprising pearl stratum powder.

10. The therapeutic composition according to claim 8, wherein the extract is from pine needles of Pinus tabulaeformis Carr.

11. The therapeutic composition according to claim 8, wherein the extract is from pine needles of Pinus massoniana Lamb.

12. The therapeutic composition according to claim 8, wherein the extract is from pine needles of Pinus yunnanensis Franch.

13. The therapeutic composition according to claim 8, further comprising Radix Puerariae extract.

14. The therapeutic composition of claim 8, further comprising an extract of Radix Puerariae, wherein the proportion of pine needle extract and Radix Puerariae extract is from 3:1 to 5:2.

15. The therapeutic composition of claim 8, further comprising pearl stratum powder, wherein the proportion of pine need extract and pearl stratum powder is from 20:1 to 2:1.

16. The therapeutic composition of claim 8, further comprising an extract of Radix Puerariae and pearl stratum powder.

17. A method of using the therapeutic composition of claim 8 to treat a disease, comprising:
    (a) orally administering the extract to adults in a dosage of 1.0 to 3.0 grams per time and three times per day; or
    (b) orally administering the extract to children of ages 5 to 14 in a dosage of 0.5 to 1.0 grams per time and three time per day; wherein the disease is selected from the group consisting of hypertension, diabetes, coronary heart disease, angina pectoris, arrhythmia, myocarditis, hyperlipidemia, high blood viscosity, high blood aggregation, cerebral infarction, arterial sclerosis, cerebral arteriosclerosis, and senile dementia.

18. A method for treating a disease, comprising the administration of a therapeutically effective amount of the composition of claim 8; wherein the disease is selected from the group consisting of hypertension, diabetes, coronary heart disease, angina pectoris, arrhythmia, myocarditis, hyperlipidemia, high blood viscosity, high blood aggregation, cerebral infarction, arterial sclerosis, cerebral arteriosclerosis, and senile dementia.

19. The method of claim 18, wherein the extract has an effect selected from reducing blood pressure, blood lipids, blood sugar, blood viscosity, and/or aggregation rate of platelets.

20. The method according to claim 18, wherein the extract is from pine needles of Pinus tabulaeformis Carr.

21. The method according to claim 18, wherein the extract is from pine needles of Pinus massoniana Lamb.

22. The method according to claim 18, wherein the extract is from pine needles of Pinus yunnanensis Franch.

23. The method of claim 18, wherein the disease is hypertension.

24. A method for treating hypertension, comprising administering a therapeutically effective amount of an extract from the pine needles of Pinus tabulaeformis Carr, wherein the extract is brown in solid state, is water-soluble and has a maximum absorption peak at about 242 nm in the ultraviolet-visible light spectrum.

* * * * *